United States Patent [19]

Capuano

[11] 4,028,197
[45] June 7, 1977

[54] METHOD FOR MONITORING AVAILABLE CHLORINE IN SWIMMING POOLS

[75] Inventor: Italo A. Capuano, Orange, Conn.

[73] Assignee: Olin Corporation, New Haven, Conn.

[22] Filed: Dec. 31, 1975

[21] Appl. No.: 645,582

Related U.S. Application Data

[63] Continuation-in-part of Ser. No. 456,088, March 29, 1974, Pat. No. 3,956,094.

[52] U.S. Cl. .............................................. 204/1 T
[51] Int. Cl.[2] ....................................... G01N 27/46
[58] Field of Search .......................... 204/1 B, 1 T

[56] References Cited

UNITED STATES PATENTS

| | | | |
|---|---|---|---|
| 2,414,411 | 1/1947 | Marks | 204/1 B |
| 2,651,612 | 9/1953 | Haller | 204/195 R |
| 2,913,386 | 11/1959 | Clark | 204/195 P |
| 3,756,923 | 9/1973 | Dahms | 204/195 R |

*Primary Examiner*—T. Tung
*Attorney, Agent, or Firm*—James B. Haglind; Donald F. Clements; Thomas P. O'Day

[57] ABSTRACT

A method for the measurement of amounts of free available halogen in solution which is independent of the pH has been developed. The method comprises providing a sensing electrode having a porous conductive component and a reference electrode in a measuring zone, and connecting a potential measuring means between the sensing electrode and the reference electrode. An aqueous solution containing an available halogen is introduced into the measuring zone to contact the sensing electrode and the reference electrode. A pH control solution is passed through at least a portion of the porous conductive component. The free available halogen concentration is measured and indicated on the potential measuring means.

Employing the method, residual amounts of an oxidizing or reducing agent in solution can be continuously measured, independent of the pH of the solution. In addition, the electrode surface is continuously cleansed by the pH control solution. The method of the present invention can be used, for example, to measure the free available chlorine concentration in swimming pool waters.

13 Claims, 2 Drawing Figures

METHOD FOR MONITORING AVAILABLE CHLORINE IN SWIMMING POOLS

This application is a continuation-in-part of application Ser. No. 456,088, filed Mar. 29, 1974, now U.S. Pat. No. 3,956,094.

This invention relates to a method for the measurement of amounts of available halogens in aqueous solutions.

In the treatment of streams with oxidizing or reducing agents, it is often desirable to monitor the residual content continuously. This measurement is usually accomplished by providing a measuring electrochemical cell at some point either preceding or following the addition of the oxidizing or reducing agent. The output of the monitoring device can then be used to provide direct readings of residual amounts of oxidizing or reducing agent.

During an oxidation-reduction reaction, electrons are transferred between an ion in the solution being measured and a sensing electrode. A second reference electrode is required to complete the circuit and transfer electrons back to the sensing electrode or to the solution by means of a second oxidation-reduction reaction. A voltage response recording or indicating device is connected between the two electrodes. The combination of the two electrodes and the liquid flowing through this measuring device forms a galvanic cell.

At the surface of the sensing electrode, it is important to provide an environment which maintains a pH controlled at the desired level. This assures a suitable reaction rate for the oxidizing or reducing agent and thus a reliable and accurate measurement for the ion being determined. Oxidation-reduction measurements are generally pH dependent and require the addition of a buffer to the solution to obtain accurate analyses.

As the buffer is added to the solution containing the oxidizing or reducing agent, sufficiently large amounts must be used to assure the desired pH condition. In recirculated systems such as the water in a swimming pool, it is undesirable to introduce relatively large amounts of material such as a buffer.

In addition, in order to make accurate measurements with measuring cells of this type, extreme cleanliness of the electrode surfaces contacting the stream is required. Heretofore, cleaning of the electrodes in measuring cells was accomplished, for example, by providing small balls within the cell to be agitated by the flowing liquid. The rolling action of the balls against the electrode surfaces kept the surfaces clean. One disadvantage of this method is that the cleaning effect of the balls is highly dependent on the liquid speed, i.e., at very low flow speeds little cleaning action would occur. A second disadvantage with the ball method is that the inlet and outlet passages of the cell must be of such a diameter as not to permit the balls to escape, since for cleaning purposes, very small balls are used. The liquid inlet and outlet passages are consequently quite restricted and often become clogged by contaminants contained in the liquid.

Other measuring cells are known in which one or both of the electrodes are rotatable by a motor. An abrasive material is added to the liquid and upon rotation of the electrodes, the abrasive contacts the electrodes so that cleaning is accomplished.

Again, wherever the liquid stream is to be recirculated, for example, in the determination of oxidizing agents in water from a swimming pool, the addition of foreign materials such as abrasives which are then returned to the main body of liquid cannot be tolerated. Furthermore, with the rotating electrode arrangement the complexity and thus the cost of the device are considerably increased.

It is also known to determine available halogens in aqueous solutions by means which apply a potential while adding a concentrated reagent to the aqueous solution. See, for example, U.S. Pat. No. 2,414,411 issued Jan. 14, 1947, to H. C. Marks. The aqueous solutions which have been treated with available halogen-containing components often contain the available halogen in two different forms, free available halogen, in the form of hypohalous acid or hypohalite ions; and combined available halogen in nitrogen-containing compounds such as haloamines where the available halogen is bonded to the nitrogen atoms. By applying energy in electrical or chemical form to the aqueous solution, combined available halogen can be converted to free available halogen. An accurate measurement of the free available halogen in an aqueous solution containing also combined available halogen cannot be made if electrical energy or chemical energy is applied to the aqueous solution.

In addition, aqueous solutions containing available halogen may also contain metallic ions such as copper and iron. Application of a voltage to these solutions can deposit these ions on one of the electrodes, interfering with the accurate determination of the available halogen.

Therefore, a method is required which will accurately determine free available halogens in an aqueous solution also containing combined available halogen.

In operation, the sensing electrode and the reference electrode are located in a measuring zone with the potential measuring device connected between the two electrodes. An aqueous solution containing the available halogen is introduced into the measuring zone where it contacts the sensing electrode and the reference electrode. The concentration of the oxidizing or reducing agent is determined at the sensing electrode and is registered on the potential measuring device. A pH control solution is passed through at least a portion of the porous conductive material component of the sensing electrode prior to and during contact with the aqueous solution.

Figure 1:
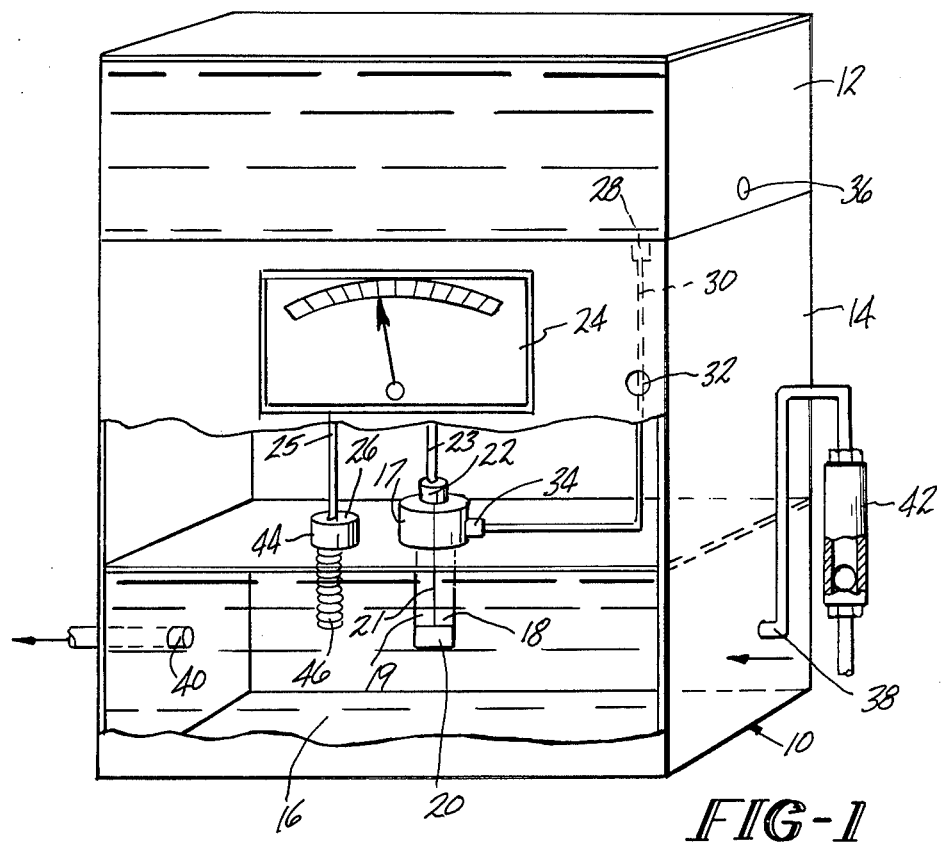
FIG. 1 is a front view of an apparatus suitable for use with the method of the present invention for measuring available halogen concentrations in aqueous solution.

The available halogen concentration measuring apparatus of FIG. 1 is housed in container 10 having pH control solution compartment 12, meter compartment 14, and electrode compartment 16. Sensing electrode 18 has an upper portion 17 and a lower portion 19. Upper portion 17 is positioned in meter compartment 14 and includes contact 22. Lower portion 19 is positioned in electrode compartment 16 and contains porous conductive material 20. Electrode wire 21 provides the electrical connection between porous conductive material 20 and contact 22. Meter 24 is connected to sensing electrode 18 by wire 23 attached to contact 22. Reference electrode 26 has housing 44 positioned in meter compartment 14 and wire spiral 46 positioned in electrode compartment 16. Inlet 38 in electrode compartment 16 permits the introduction of an aqueous solution whose available halogen concentration is to be measured by sensing electrode 18. The aqueous solution then contacts reference electrode 26 and leaves compartment 16 through outlet 40. The pH control solution in compartment 12 can be removed through outlet 36. Flow rate control valve 42 regulates the flow of solution into electrode compartment 16.

Figure 2:
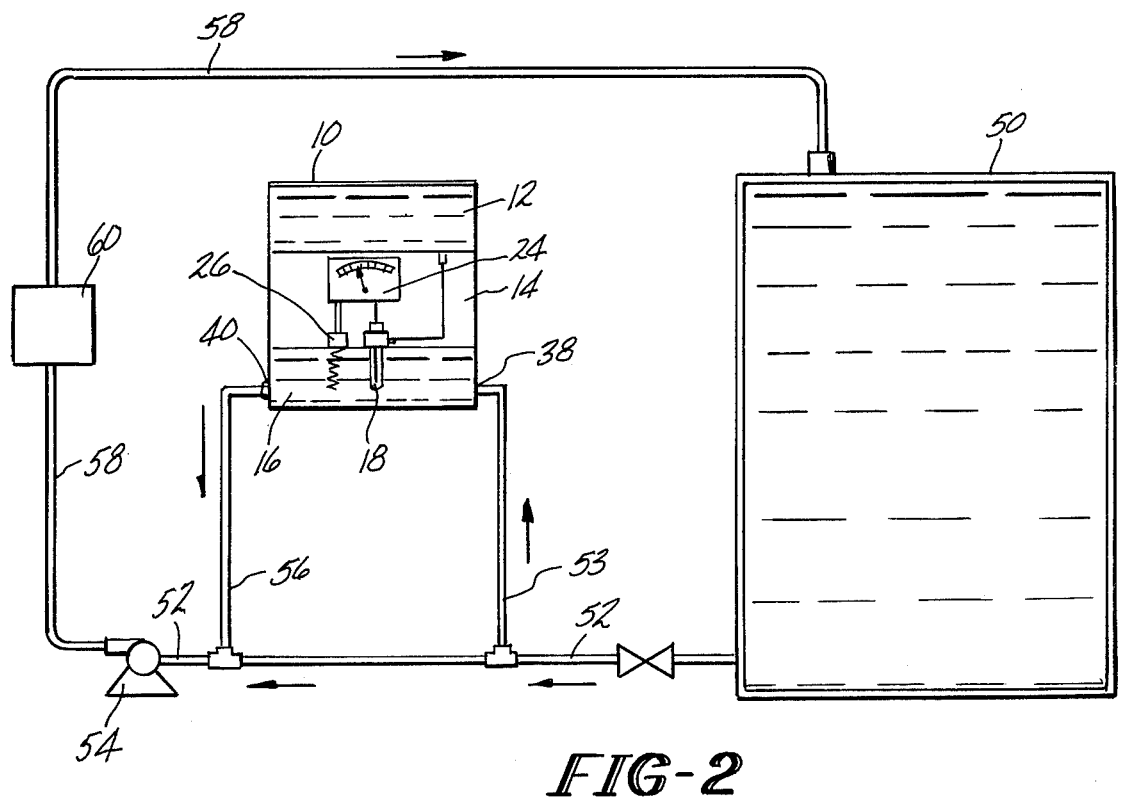
FIG. 2 is a diagramatic plan of a swimming pool circulating system incorporating the apparatus of FIG. 1.

FIG. 2 illustrates the use of the apparatus of FIG. 1 measuring available halogen concentration in water from a swimming pool system including swimming pool 50. A pump 54 is connected at its low pressure or suction side to pool 50 by conduit 52. Also connected to conduit 52 is conduit 53 which circulates a portion of the pool water from 52 through measuring cell 10. The stream of pool water enters the electrode compartment 16 through inlet 38, contacting sensing electrode 18 and reference electrode 26, and leaving compartment 16 through outlet 40. The stream returns to conduit 52 via conduit 56 to be recirculated by pump 54 through filter 60 and to pool 50 by conduit 58. When pool 50 is treated with a compound containing available chlorine for example, calcium hypochlorite, the concentration of the hypochlorite ion in the water is determined by measuring cell 10. Hypochlorite ions in the solution entering electrode compartment 16 contact sensing electrode 18 and react according to equation (a) below. The potential generated by this reaction is measured by the electrode and indicated on meter 24, the meter being calibrated to give a direct reading of the hypochlorite ion concentration in the stream from the swimming pool.

The sensing electrode used in the method of the present invention has as a component a porous conductive material. Suitable materials useful as the porous conductive material include graphite, metal compounds such as tantalum carbide, tungsten carbide, zirconium carbide, niobium carbide, tantalum silicide, tungsten silicide, vanadium silicide, niobium silicide, titanium nitride, zirconium nitride, molybdenum silicide, tantalum boride, titanium boride, zirconium boride, hafnium boride, molybdenum boride, chromium boride, and niobium boride, and sintered metals, for example, iron, steel, copper, nickel, platinum, gold, chromium and tantalum.

The electrodes can be in any convenient form; for example, a disc, cylinder or tube. In one embodiment, sensing electrode 18 is comprised of a plastic tube having a disc or porous conductive material 20 at one end. A conductive metal wire 21 is attached to the upper side of porous conductive material 20 and extends through the tube to a terminal. The terminal seals the other end of the tube and comprises the contact for wire lead 23 to meter 24. An opening in the upper part of the tube permits pH control solution to pass through the tube contacting the upper portion of the porous conductive material. The pH control solution does not directly come in contact with the solution containing the available halogen until it has passed through at least a portion of porous conductive material 20. The flow of the pH control solution through the porous conductive material is small and controlled so that the porous conductive material is continually cleansed by the solution. The rate of flow of the pH control solution through the porous conductive material is controlled in part by the porosity of the porous material and in part by the pressure of the flow of electrolyte into the electrode compartment. The rate of flow of pH control solution through the porous conductive material is from about 0.01 to about 0.1 ml per minute, and preferably from about 0.02 to about 0.05 ml per minute.

The portion of porous conductive material through which the pH control solution flows can be any suitable part as along as it includes the surface of the porous conductive material which is in contact with the aqueous solution containing the available halogen.

The pH control solution used can be any acid or base which does not adversely react with the electrode materials or the available halogen being determined. Where the available halogen is being recirculated it is preferred that the pH control solution be one which introduces no foreign materials into the system. For example, where the oxidizing agent is available chlorine in the form of hypochlorite ion, suitable pH control agents include hydrochloric acid, alkali metal chlorides and sodium carbonate. When hydrochloric acid is the pH control agent, a solution containing from about 0.5 to about 6 percent by weight of HCl can be employed.

Also suitable as pH control solutions are mixtures of acids or bases with inorganic salts. For example, in the measurement of available chlorine a suitable mixture is that of hydrochloric acid with an alkali metal chloride in which the hydrochloric acid is from about 0.5 to about 6 percent by weight and the alkali metal chloride is from about 0.001 to about 10 percent by weight. The alkali metal chloride can be for example, sodium chloride, potassium chloride or lithium chloride. Aqueous solutions containing available halogens selected from the group consisting of chlorine, iodine and bromine can be used with the apparatus and method of the present invention. The available halogen is suitably present in concentrations of from about 0.1 to about 20 parts per million and, preferably from about 0.5 to about 5 parts per million.

As shown in FIG. 2, the method of the present invention can be used, for example, to determine free available chlorine, or hypochlorite ion, in swimming pool water. The reaction at the sensing electrode is expressed by equation (a) as follows:

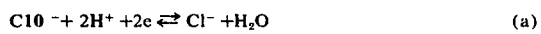

$$ClO^- + 2H^+ + 2e \rightleftarrows Cl^- + H_2O \qquad (a)$$

While the pH control solutions are normally aqueous solutions other solvents may be used if desired.

The reference electrode can be any known convenient electrode or electrode system. The reference electrode can be, for example, a metal wire or it may be a metal wire used in conjunction with an electrolyte connected through a salt bridge.

The measuring zone into which the solution containing the available halogen to be determined is introduced may be any suitable zone such as electrode compartment 16 shown in FIG. 1 or, for example, a container such as a section of pipe or tubing in which both the sensing electrode and the reference electrode are secured in position and spaced apart.

The method of the present invention is suitable for use with solutions of available halogens at temperatures up to about 150° F. By employing the internally pH controlled electrode of the present invention measurement of the available halogen in the solutions is independent of the pH of the solution itself.

Thus the method of the present invention permits the measurement of the concentration of an oxidizing agent such as the free available halogen or peracetic acid in aqueous solutions.

Typical compounds whose aqueous solutions provide the free available halogens are chlorine, bromine or iodine include alkali metal hypohalites, alkaline earth hypohalites, and hypohalous acids. Sodium, potassium, and lithium are alkali metals whose salts can be employed. Suitable alkaline earth metals include calcium, magnesium, strontium and barium.

To accurately determine, for example, the free available chlorine concentration in aqueous solutions, that is the chlorine present as hypochlorous acid or hypochlorites, it is desirable that no potential be applied between the reference electrode and the sensing electrode while employing the method of the present invention. Aqueous solutions, such as swimming pool water, often contain nitrogen-containing substances, such as ammonia, urine or perspiration (urine and perspiration contain the compound urea as one of their components). When aqueous solutions containing these nitrogen-containing substances are treated with free available chlorine, some of the chlorine reacts with the nitrogen atoms of these substances to form compounds broadly classified as "chloramines". Chloramines derived from ammonia or urea are undesirable in aqueous solutions as they cause unpleasant odors, and in the case of swimming pool waters, cause eye irritation to swimmers. In contrast to free available chlorine, chlorine which is bonded to the nitrogen atoms of a chloramine is referred to as combined available chlorine. An effective way of destroying undesirable chloramines is to react them with additional free available chlorine. The application of an electrical potential to an aqueous solution containing chloramines will, in many cases, release the chlorine from the nitrogen atom and the available chlorine is no longer combined, but becomes free available chlorine. A method of measuring free available chlorine which applies a potential to an aqueous solution containing chloramines which is sufficient to release the chlorine will obtain readings for free available chlorine which are inaccurate. Thus it can be seen that the accurate measurement of free available chlorine aqueous solutions by the method of the present invention in which no potential is applied, will not be effected by the presence of compounds such as chloramines having combined available chlorine.

It may be desirable to apply a potential in using the method of the present invention, for example, should you want to measure the concentration of chloramines in aqueous solutions containing free available chlorine. The free available chlorine present in the solution is first determined in the absence of an applied potential. A potential is then applied to the aqueous solution which is sufficient to release the combined available chlorine of chloramines as free available chlorine and a second measurement of this free available chlorine is now taken. The difference between the two readings represents the combined available chlorine (chloramine) and this information may be used to modify the treatment of the aqueous solution, for example, to destroy the chloramines present.

The above discussion has been presented in terms of chloramines but halogens such as bromine or iodine also react with nitrogen to form bromamines or iodamines in which the halogen is in the combined available form.

In addition, available halogen compounds where the halogen is bonded to nitrogen atoms as combined available halogen but which release the halogen atoms as free hypochlorous acid when dissolved in a solvent such as water, in the absence of applied energy may be determined by the method of the present invention. Typical compounds include haloisocyanuric acids such as dichloroisocyanuric acid or trichloroisocyanuric, alkali metal haloisocyanurates and alkaline earth metal haloisocyanurates where the alkali metals and alkaline earth metals are defined as above.

Chlorine and bromine are preferred free available halogens with chlorine being particularly prepared. Solutions containing free available chlorine are solutions of compounds selected from the group consisting of alkali metal hypochlorites, alkaline earth metal hypochlorites, alkali metal chloroisocyanurates alkaline earth chloroisocyanurates and hypochlorous acid.

Suitable applications for the method of the present invention include the determination of available halogens in water supplies treated with available halogen for sanitation purposes; the detection of available halogen leaks during the production of the halogens, for example, in process lines such as cooling water lines; and the monitoring of available halogens in effluent streams where their presence may be undesirable.

The improved method of the present invention can also be used to determine concentrations of reducing agents in aqueous solutions. Typical reducing agents which can be determined include sulfur dioxide, alkali metal and alkaline earth metal dithionites, and alkali metal and alkaline earth metal sulfites among others.

In using a porous conductive material as the sensing electrode, the pH control solution can be passed through at least a portion of the electrode to:
1. maintain the measurement of the available halogen concentration independent of the pH of the solution while adding a minimal amount of control solution.
2. continuously provide self-cleaning of the electrode.

The following examples are presented to illustrate the invention more fully. All parts and percentages are by weight unless otherwise indicated.

EXAMPLES 1 – 6

The measuring cell substantially as shown in FIG. 1 was connected to a tank having a recirculation system.

Measuring cell was comprised of a pH control solution compartment, a meter compartment and an electrode compartment, each made of a transparent plastic material. A sensing electrode was comprised of a plastic tube having at one end a disc of porous graphite. A platinum wire extended from the top of the porous graphite disc to the meter contact to conduct electrons are generated in the reaction at the sensing electrode. A pH control solution, containing 3 percent hydrochloric acid and 0.5 percent potassium chloride in water, was fed through the porous graphite disc at a rate of 0.02 ml. per minute to cleanse the disc and to maintain a constant pH at the electrode surface. The tank, having a capacity of 200 liters, was filled with water. The tank was connected to the suction side of a pump to circulate the solution from the tank at a rate of 25 liters per minute. A portion of this solution, about 0.2 to 1 liter per minute, was circulated through the measuring cell. The reference electrode comprised a silver wire connected by a natural fiber salt bridge to a silver chloride electrolyte. A microammeter was used to detect current generated at the sensing electrode. The temperature of the tank water was maintained at 35° C. and the pH at 7.75. In a series of experiments varying amounts of calcium hypochlorite were added and dissolved in the water to form solutions containing available chlorine in the form of the hypochlorite ion. The concentration of available chlorine present in each solution was measured by the method and apparatus of the present invention. The results of Examples 1–6 are given in Table 1 below.

Table I

Determination of Available Chlorine Concentration (parts per million) In Calcium Hypochlorite Solutions

| Example No. | Ortho-tolidine colorimetric determination | Measuring cell of the present invention |
|---|---|---|
| 1 | 0.5 | 0.45 |
| 2 | 1.0 | 0.95 |
| 3 | 1.7 | 1.7 |
| 4 | 2.5 | 2.5 |
| 5 | 4.2 | 4.0 |
| 6 | 4.9 | 5.0 |

Results of the above examples show that determination of available chlorine by the measuring cell of the present invention is as good as that obtained by the ortho-tolidine colorimetric method widely used for the measurement of available chlorine in swimming pool waters.

EXAMPLES 7–11

Using the same apparatus of Examples 1–6, the tank was filled with water and varying amounts of sodium dichloroisocyanurate dissolved to form solutions containing available chlorine. The available chlorine concentration was determined by both the ortho-tolidine colorimetric method and the measuring cell of the present invention. The results are given in Table 2.

For comparative purposes, the available chlorine content was determined using a commercially available specialty kit employing a conventional colorimetric determination method using an orthotolidene solution. The method is described in "Standard Methods for the Examinations of Water and Waste Water..., 11 th edition," American Public Health Association, Inc., 1960, pp. 103–105. This method is commonly used to determine the available chlorine content of swimming pool water and is accurate to about 0.1 parts per million of available chlorine.

Table 2

Determination of Available Chlorine (parts per million) in Sodium Dichloroisocyanuate solutions

| Example No. | Ortho Tolidine Colorimetric Determination Concentration | Measuring Cell of the Present Invention |
|---|---|---|
| 7 | 1.2 | 1.4 |
| 8 | 2.4 | 2.3 |
| 9 | 2.8 | 2.7 |
| 10 | 4.0 | 4.2 |
| 11 | 5.0 | 4.9 |

These examples illustrate that the method and apparatus of the present invention can be used to determine available chlorine using organic compounds as sources of available chlorine as well as inorganic compounds such as calcium hypochlorite. The analyses by the method using the measuring cell are as good as those obtained with the colorimetric method.

EXAMPLES 12–15

Using the apparatus of Examples 1–6, four batches of water, each at a different temperature, were separately added to the tank. Calcium hypochlorite was dissolved in each batch to prepare a solution containing available chlorine. The available chlorine concentration was measured by both the ortho-tolidine method and using the measuring cell of the present invention. The results are given in Table 3 below.

Table 3

Effect of Temperature on the Determination of Available Chlorine (parts per million)

| Example No. | Pool Temperature (° F) | Ortho-tolidine Method | Measuring Cell of the Present Invention |
|---|---|---|---|
| 12 | 93.2 | 3.5 | 3.7 |
| 13 | 89.6 | 2.4 | 2.4 |
| 14 | 77.0 | 2.0 | 2.2 |
| 15 | 68.0 | 1.3 | 1.4 |

The above examples show that a change in temperature of an aqueous solution containing available chlorine has no effect on the ability of the measuring cell of the present invention to accurately determine the available chlorine concentration.

EXAMPLES 16–20

Using the same apparatus as in the previous Examples, the tank was filled with water and sufficient calcium hypochlorite added to give an available chlorine concentration of 3.0 parts per million. Concentrated hydrochloric acid and sodium carbonate were added to this solution to change the pH of the solution over a range of values. A pH meter was used to determine the actual pH of the solution. The results are given below in Table 4.

Table 4

Effect of pH on the Determination of Available Chlorine in Aqueous Solutions

| Example No. | pH | Available Chlorine (ppm) |
|---|---|---|
| 16 | 6.5 | 3.0 |
| 17 | 7.0 | 3.0 |
| 18 | 7.5 | 3.0 |
| 19 | 8.0 | 3.0 |
| 20 | 8.5 | 3.0 |

These examples show that changing the pH of the solution over a range of values has no effect on the ability of the measuring cell of the present invention to accurately determine available chlorine concentrations.

Comparative Examples A–E

Examples 16–20 were repeated without supplying the pH control solution to the sensing electrode. The pool water contained 1.0 parts per million of available chlorine, obtained by dissolving calcium hypochlorite. The results are given in Table 5.

Table 5

Effect of pH on the Determination of Available Chlorine In Aqueous Solutions Using an Electrode Having No pH Control

| Comparative Example No. | pH | Available Chlorine (ppm) |
|---|---|---|
| A | 6.5 | 1.4 |
| B | 7.0 | 1.2 |
| C | 7.5 | 1.1 |
| D | 8.0 | 1.0 |
| E | 8.5 | 0.7 |

These examples show that there is considerable variation in the available chlorine determination when the pH of the aqueous solution is changed and without supplying a pH control solution to the electrode of the present invention.

EXAMPLES 21–22

Using the apparatus of Examples 1–6 aqueous solutions of varying concentrations of available chlorine were prepared by dissolving calcium hypochlorite in the water. In addition, chloramine was generated in the tank by the addition of ammonium chloride to the tank water. To accurately determine free available chlorine by the ortho-tolidine colorimetric method in the presence of chloramine, the water sample was chilled to 2° C prior to addition of the ortho-tolidine reagent. The results of this experiment are given in Table 6.

Table 6

Effect of Chloramine on the Determination of Available Chlorine (ppm) in Aqueous Solutions of Calcium Hypochlorite

| Example No. | Total Available $Cl_2$ by Ortho-Tolidine Analysis (25° C) | Free Available $Cl_2$ by Ortho-Tolidine Analysis (2° C) | Free Available $Cl_2$ by Measuring Cell of the Present Invention (25° C) |
|---|---|---|---|
| 21 | 1.0 | 0.2 | 0.2 |
| 22 | 5.0 | 0.5 | 0.5 |

The above examples show the ability of the method and apparatus of the present invention to readily and accurately determine the available chlorine concentration in an aqueous solution of calcium hypochlorite in the presence of chloramine and in the absence of an applied voltage.

EXAMPLES 23–29

Using the apparatus of FIGS. 1 and 2, a series of impurities often found in swimming pool water were added to aqueous solutions of available chlorine prepared from calcium hypochlorite to determine the effect of these impurities on the accurate determination of the available chlorine concentration using the measuring cell of the present invention. In each of the examples, the impurity was added to the aqueous solution of calcium hypochlorite and the pH and temperature of the tank water determined. The results of the examples are given in Table 7.

Examples 23–29 illustrate that in the presence of a large variety of impurities often found in swimming pools, an accurate measurement of the available chlorine content by the novel method and measuring cell of the present invention is not materially effected.

EXAMPLE 30

Using the apparatus illustrated in FIGS. 1 and 2, the measuring cell of the present invention was used to determine the available chlorine content of water for 6 successive days in a recirculation system for a swimming pool having a capacity of 22,000 gallons. The measuring cell was installed on the vacuum side of the recirculation pump. The pH of the pool water was maintained at 7.6 and the pool temperature at 65° F. The available chlorine concentration was determined by both the ortho-tolidine colorimetric method and using the measuring cell of the present invention. The results are given in Table 8.

Table 8

Determination of Available Chlorine (parts per million) In An In-Ground Swimming Pool Containing Aqueous Solutions of Calcium Hypochlorite

| Day | Ortho-Tolidine Method | Measuring Cell of the Present Invention |
|---|---|---|
| 1 | 0.70 | 0.75 |
| 2 | 0.30 | 0.30 |
| 3 | 0.50 | 0.50 |
| 4 | 0.70 | 0.72 |
| 5 | 0.80 | 0.90 |
| 6 | 0.60 | 0.70 |

The above example illustrates the ability of the method and apparatus of the present invention to accurately determine the residual available chlorine content in the water of a swimming pool employing a recirculation system.

What is claimed is:

1. A method for measuring the available halogen concentration of an aqueous solution in the absence of an applied potential comprising:
   1. providing a sensing electrode having a porous conductive component and a reference electrode in a measuring zone,
   2. connecting a potential measuring means between said sensing electrode and said reference electrode,
   3. introducing said aqueous solution containng said available halogen into said measuring zone,
   4. contacting said porous conductive component of said sensing electrode and said reference electrode Table 7

Effect of Various Impurities on the Determination of Available Chlorine (parts per million) in Aqueous Solutions of Calcium Hypochlorite

| Example No. | Impurity | Impurity Conc. (ppm) | Pool pH | Pool Temp. F° | Available $Cl_2$ by Ortho-Tolidine Method | Available $Cl_2$ by measuring Cell of the Present Invention | Effect of Impurity on the Available $Cl_2$ Measurement by the Measuring Cell of the Present Invention |
|---|---|---|---|---|---|---|---|
| 23 | CHLORATE ($NaClO_3$) | 78 | 7.5 | 91.4 | 2 | 2 | None |
| 24 | SULFATE ($Na_2SO_4$) | 67.5 | 7.7 | 90 | 1.8 | 1.8 | None |
| 25 | COPPER ($CuSO_4$) | 6.4 | 7.7 | 90 | 1.8 | 1.8 | None |
| 26 | CALCIUM ($CaCl_2$) | 36 | 7.3 | 88 | 1.5 | 1.5 | None |
| 27 | IRON ($FeCl_3$) | 16.5 | 8.6 | 90 | 3.6 | 3.6 | None |
| 28 | CYANURIC ACID | Saturated, added 50 ppm | 7.2 | 90 | 3.7 | 3.8 | Negligible |
| 29 | Alkyldimethyl Dichloro Benzyl Ammonium Chloride* | 10 | 7.2 | 82 | 3.8 | 3.8 | None |

*Commercial algaecide sold under the trademark Aquatech by the Aquatech Corporation with said aqueous solution containing available halogen, 5. passing a pH control solution through at least a portion of said porous conductive component of said sensing electrode, said pH control solution cleansing said portion of said porous conductive component and said pH control solution controlling the pH at said surface of said portion of said porous conductive component contacting said aqueous solution containing said available halogen, 6. measuring said available halogen concentration in said aqueous solution, and 7. indicating said available halogen concentration on said potential measuring means.

2. The method of claim 1 in which said available halogen is selected from a group consisting of chlorine, bromine, and iodine.

3. The method of claim 2 wherein said available halogen is chlorine.

4. The method of claim 3 in which said aqueous solution is a solution of a compound containing said available chlorine selected from a group consisting of alkali metal hypochlorites, alkaline earth metal hypochlorites, alkali metal chloroisocyanurates, alkaline earth metal chloroisocyanurates, hypochlorous acid and chloroisocyanuric acids.

5. The method of claim 4 in which said compound is an alkaline earth metal hypochlorite.

6. The method of claim 5 in which said alkaline earth metal hypochlorite is calcium hypochlorite.

7. The method of claim 4 in which said aqueous solution contains hypochlorous acid.

8. The method of claim 4 in which said pH control solution is hydrochloric acid containing from about 0.5 to about 6 percent by weight of HCl.

9. The method of claim 8 in which the rate of flow of said pH control solution thru said portions of said porous conductive component is from about 0.01 to about 0.1 ml. per minute.

10. The method of claim 9 in which said porous conductive component is graphite.

11. The method of claim 4 in which said hydrochloric acid contains from about 0.001 to about 10 percent by weight of an alkali metal chloride.

12. The method of claim 2 in which said aqueous solution containing said available halogen is swimming pool water.

13. The method of claim 2 in which said available halogen concentration in said aqueous solution is from about 0.1 to about 20 parts per million.

* * * * *